United States Patent [19]
Barry

[11] Patent Number: 5,928,136
[45] Date of Patent: Jul. 27, 1999

[54] ARTICULATED VERTEBRA FOR ENDOSCOPES AND METHOD TO MAKE IT

[75] Inventor: James P. Barry, Charlton, Mass.

[73] Assignee: Karl Storz GmbH & Co., Tuttlingen, Germany

[21] Appl. No.: 08/800,733

[22] Filed: Feb. 13, 1997

[51] Int. Cl.⁶ .......................................................... A61B 1/04

[52] U.S. Cl. ............................................ 600/142; 600/139

[58] Field of Search .................................... 600/139, 140, 600/141, 142, 143, 144, 146, 149; 138/120

[56] References Cited

U.S. PATENT DOCUMENTS 4,805,596  2/1989  Hatori .

*Primary Examiner*—Beverly M. Flanagan
*Attorney, Agent, or Firm*—Donald D. Mon

[57] ABSTRACT

A vertebra for an endoscope and a joinder for segments of the vertebra. A pair of tubular segments have tangs that overlap one another. One tube is imperforate and the other is perforate, with a hinge aperture through it. The perforate tang has a dimension of thickness. A hinge pin is adhered to the imperforate tang and passes into the aperture. Its length is less than the thickness of the perforate tang so no part of the pin projects beyond the perforate tang. Preferably the pin is welded to the imperforate tang.

8 Claims, 1 Drawing Sheet

ARTICULATED VERTEBRA FOR ENDOSCOPES AND METHOD TO MAKE IT

FIELD OF THE INVENTION

An articulated vertebra for an endoscope which supports its elements and provides for limited in-plane bending.

BACKGROUND OF THE INVENTION

So-called flexible endoscopes include means for illumination of a field to be studied, an optical system to observe the field, and means to cause controlled bending of the endoscope. The elements which relate to illumination and observation are usually in the nature of flexible optical fibers. Especially the fibers used for observation are generally very small in size and large in number. They require lateral support and enclosure to maintain an orderly array, and to reduce the rate of breakage of the fibers.

These elements and their support must together form an endoscope of minimal diameter. Endoscopes are frequently inserted into very small passages and orifices, and any reduction in lateral dimensions, not made at the cost of reduction of reliability or function, is welcome.

Articulations comprising short segments of tubing that are pivotally jointed together are known. Customarily they are joined by headed rivets which act as pivots. These joinder means involve either an enlargement on the outside of the vertebra, or on its inside, and sometimes on both. On the inside it reduces the cross-section which accommodates the endoscope elements, and thereby requires a larger tube diameter for an equivalent result. On the outside it contributes an enlargement or disruption. Either way, the result is a larger-diameter endoscope.

Alternate joinder means of the short segments are also known and include interlocking tab type designs, stay wire type designs, ball and socket designs, and others. These joinder means also involve an enlargement of the vertebrae joint.

It is an object of this invention to provide an articulated tubular vertebra without objectionable protuberances either inside or outside of the pivot means which joins the tubular segments, whereby to provide joinders and joints of minimal radial dimension (thickness), and thereby an articulation of minimal external diameter for a given useful internal diameter.

BRIEF DESCRIPTION OF THE INVENTION

An articulated vertebra according to this invention comprises a plurality of pivotally serially joined tubular segments. Together, the segments form an internal passage to receive elements of an endoscope, such as optical fibers and control wires. Each segment has an inside wall and an outside wall, the inside walls forming the passage.

Each segment other than the two end segments of the vertebra includes a first tang on one end and a second tang on the other end of the segment. These tangs may be flattened, and one may be joggled so as to fit slidably inside the other. One of the tangs has a hinge aperture formed therein which overlaps the other tang.

According to a feature of this invention the joinder is completed by a hinge pin which is attached to the imperforate tang and which projects into the hinge aperture making a close fit with it. The hinge pin does not appreciably protrude beyond the perforate tang. Neither does it penetrate the inner tang. The hinge pin thereby does not adversely interfere with a surrounding sheath or tissue and the joinder causes only minimal radial enlargement.

According to a feature of this invention, retention of the hinge aperture is assured by using material of sufficient rigidity that even in the very small thicknesses involved, lateral forces will not deform the structure sufficiently to remove the outer tang from the hinge pin.

According to a preferred but optional feature of this invention, the said rigidity is assured by making the segments of a metal having a modulus of elasticity of at least 175,000 psi. Wall thicknesses on the order of 0.004 inches are contemplated.

Another feature of this invention is the method of making this joinder. According to this method, the inner tang is first slid inside the outer tang and positioned with the aperture placed precisely over the imperforate tang where the hinge pin is to be located. Then the hinge pin is inserted into the hinge aperture, and its flat surface is forced into abutment with the other tang, and is then permanently secured to it so as to form a pivoted joinder of the two adjacent tubular segments.

According to a preferred but optional feature of the invention, the pin is electrically spot-welded to the tang. It may, instead be adhesively attached to it, but welding is generally to be preferred.

According to yet another preferred but optional feature of the invention, the pin is reduced in length after the joinder by being surface-ground smooth with the other tang. Some protrusion of the exposed end of the pin is to be expected, even when ground. This does leave a small overhanging end portion, but it is so small as not to impede the smooth entry of the endoscope into and out of a sheath, or into and out of tissue. In fact, when the reduction in length is caused by grinding, the free end of the pin will be slightly "smeared" over the adjacent boundary of the aperture, and in effects forms a partial head.

To form a complete vertebra, an end segment is joined to each end of at least one segment, one having an inner tang, and the other an outer tang, their remaining ends being shaped according to the requirements of the respective endoscope. Generally there will be at least three serially joined segments in an endoscope of practical length.

The above and other features of this invention will be fully understood from the following detailed description and the accompanying drawings, in which:

DETAILED DESCRIPTION OF THE INVENTION

Figure 1:
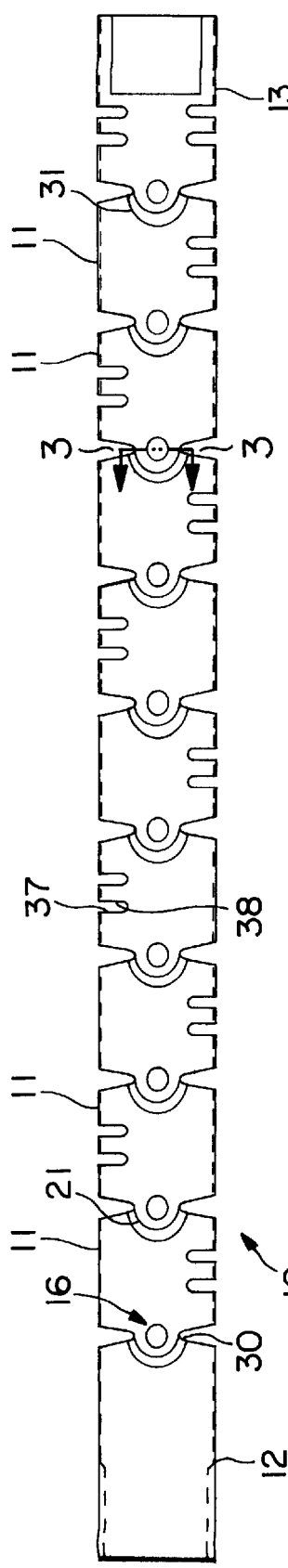
FIG. 1 is a side view of the presently-preferred embodiment of the invention.

An articulated vertebra 10 according to the invention is shown in FIG. 1. It comprises a plurality of pivotally joined-together segments 11, which are identical to one another. A first end segment 12 and a second end segment 13 complete the vertebra. Segments 12 and 13 have some parts included in segments 11, and are modified to suit the respective endoscope with which they are to be used. They are pivotally joined to respective ends of the series of segments 11.

Segments 11 are tubular metal structures. They are joined to one another by pairs of coaxial hinge pins 16. In the illustrated vertebra, all of the hinge pins are parallel to one another. This enables the vertebra to bend in only one plane, the plane of FIG. 1. Should more flexibility be desired, alternate pairs of hinge pins could be placed in planes normal to the plane of the others, so that flexibility in two planes is possible. Generally flexibility will be desired in only one plane.

Each of segments 11 has a pair of recessed ends so as to form tangs 20, 21, one at each end. In the preferred embodiment, a first of these tangs 20 is deformed inwardly, and has a flattened surface 22 that faces a flat surface 23 on the adjacent tang 21 which may be axially curved, but may instead be flat.

One of these tangs, preferably but not necessarily outer tang 21 is pierced by a hinge aperture 24 (the "perforated" tang). The other tang is not pierced (the "imperforate" tang), and when the segments are placed together, the aperture overlays surface 22. The facing surfaces are functionally parallel to one another, even though when tang 21 is curved they are not flat against each other. The tangs are sufficiently tapered so that substantial in-plane bending of the vertebra is possible without interference between adjacent tangs. The tangs are parallel when both are flat. When one is curved, its axially extending surfaces or edges will permit and guide the in-plane rotation.

Figure 3:
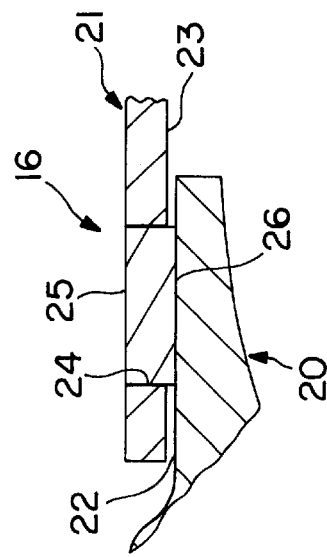
FIG. 3 is a fragmentary cross-section taken at line 3—3 in FIG. 1.

The joinder is completed by hinge pins 25, as best shown in FIG. 3. The illustrated hinge 26 is preferably provided twice at each joinder, at diametrically opposite sides of the segment.

Pins 25 are circularly shaped, and fit in respective apertures, with a fit that permits rotational movement of the segments. Each pin has a flat end surface 26 which is joined to the imperforate one of the tangs. Although any suitable means to attach the pins may be used, even including adhesives, it usually will be preferred to weld the pin to the respective surfaces. Electrical spot welding is a suitable means.

For handling of the pin, and to provide an electrical connection for spot welding, the initial length of the pin will be much greater than its final length. This additional length is removed after the joinder is completed by reducing the length of the pin. Because of the way the aperture is formed, its wall will usually be somewhat tapered, enlarging towards its outer end. During assembly, the pin will usually be expanded somewhat and thereby form a retention means.

In addition the end of the pins will be ground nearly flush with the tang through which it passes to reduce the pin's length. It will be noted that there is no substantial head on either end of the pin, although a protuberance of one or two thousandths of an inch is tolerable.

In order to prevent one segment from being snapped loose from a pin by lateral deformation, the segments are made very stiff, especially in view of the fact that the tubing is usually on the order of only about 0.004 inches in wall thickness. A modulus of elasticity of at least 175,000 psi will assure this integrity.

End segment 12 has only an imperforate tang 30. End segment 13 has only a perforate tang 31, so they effectively join to respective ends of segments 11, which are, of course different. They are also different at their extreme ends, to satisfy the requirements of the endoscope with which the vertebra is used.

Figure 2:
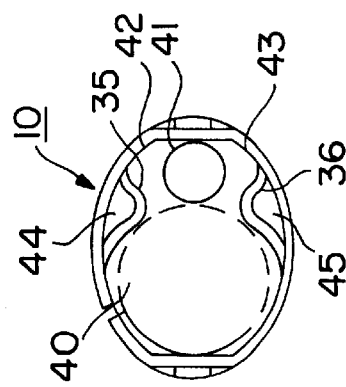
FIG. 2 is a right-hand end view of FIG. 1.

Guides 35, 36 are formed from portions of the wall of the segments that are freed for inward deformation by slits 37, 38. As best seen in FIG. 2, these are shaped to guide various parts of the endoscope inside the passage.

Circle 40 schematically shows a working channel for accommodating instrumentation. Circle 41 schematically shows a channel for a fiber optic bundle for forwarding an image. Circles 42, 43 schematically show light guides. Circles 44, 45 schematically show articulation cables.

An ovular or circular vertebra having a minor outer dimension of as small as 1.952 mm, and 2.570 mm without undesirable protrusions which could adversely increase the diameter of the endoscope or interfere with passage into and out of the sheath or into an out of tissue, using material with a wall thickness as small as 0.10 mm can readily be produced.

This invention is not to be limited by the embodiment shown in the drawings and described in the description, which is given by way of example and not of limitation, but only in accordance with the scope of the appended claims.

I claim:

1. A joinder for joining two adjacent segments of a vertebra for an endoscope, comprising;

a pair of tubular segments each having an axis with tangs of adjacent segments overlapping one another, one of said tangs being imperforate, and the other being perforate, having a hinge aperture therethrough which overlays a portion of the imperforate one of said tangs, the perforate tang having a dimension of thickness; and an unheaded hinge pin having an axis and an axial length no longer than said thickness, said pin passing into said aperture normal to the axis of its respective segment, said pin having one of its ends attached to its respective imperforate tang, said pin having no portion projecting beyond said its respective perforate tang said segments being sufficiently stiff that the pin cannot be removed from the aperture by deformation of the segments.

2. Apparatus according to claim 1 in which said pin is attached to said imperforate tang by welding.

3. In combination:

at least three segments according to claim 1 in which each said segment has a pair of said tangs at each of its ends, a pair of said pins joining adjacent segments at each end, the axes of all of said pivot pins being parallel.

4. A combination according to claim 3 in which portions of said segments are inwardly deformed to form guides for elements of an endoscope.

5. An endoscope vertebra comprising:

at least three adjacent tubular segments, each having a tang at each end, one of said tangs overlapping its adjacent tang, one of said tangs being flat and imperforate, the other tang being perforate, having a hinge aperture therethrough said perforate tang having a dimension of thickness, said aperture overlapping at least part of the imperforate tang;

an unheaded hinge pin attached to each imperforate tang and passing through its respective hinge aperture, the free end of said pin having no portion protruding beyond the surface of the perforated tang which would substantially interfere with axial movement of the vertebra in a sheath or in tissue.

6. Apparatus according to claim 5 in which said pin is attached to said tang by welding.

7. Apparatus according to claim 5 in which the segments are metallic, and have a modulus of elasticity at least 175,000 psi.

8. Apparatus according to claim 5 in which each of said at least three segments has a portion of its wall deformed inwardly to guide endoscope elements therein.

* * * * *